United States Patent [19]
Zeoli-Jones

[11] Patent Number: 5,480,418
[45] Date of Patent: Jan. 2, 1996

[54] THERMAL TRANSFER HAIR TREATMENT CAP

[76] Inventor: Alyce Zeoli-Jones, 18400 River Rd., Poolesville, Md. 20837

[21] Appl. No.: 208,518

[22] Filed: Mar. 11, 1994

[51] Int. Cl.$^6$ .................................................. A61F 7/00
[52] U.S. Cl. ........................................ 607/110; 607/114
[58] Field of Search ..................... 607/96, 104, 108–112, 607/114

[56] References Cited

U.S. PATENT DOCUMENTS

| | | |
|---|---|---|
| H759 | 4/1990 | Jones ........................................ 607/114 |
| 1,710,882 | 4/1929 | Larson . |
| 1,737,460 | 11/1929 | Johnson . |
| 1,751,573 | 3/1930 | Bishinger . |
| 2,420,358 | 5/1947 | Culligan et al. . |
| 2,431,882 | 12/1947 | Morten . |
| 2,453,179 | 11/1948 | Austin . |
| 2,470,833 | 5/1949 | Moore . |
| 2,488,793 | 11/1949 | Amerkan . |
| 2,493,363 | 1/1950 | Sapp . |
| 2,497,301 | 2/1950 | Farmer . |
| 2,680,305 | 6/1954 | Reed . |
| 2,718,068 | 9/1955 | Reed . |
| 2,745,192 | 5/1956 | Crise . |
| 2,783,806 | 3/1957 | Andreadis . |
| 2,804,695 | 9/1957 | Scott . |
| 2,919,494 | 1/1960 | Runci . |
| 2,945,115 | 7/1960 | Weitzel . |
| 2,997,792 | 8/1961 | Straus, II . |
| 3,148,957 | 9/1964 | Ballard . |
| 3,320,682 | 5/1967 | Sliman . |
| 3,437,095 | 4/1969 | Scott et al. . |
| 3,463,161 | 8/1969 | Andrassy . |
| 3,594,915 | 7/1971 | Routledge . |
| 3,988,568 | 10/1976 | Mantell . |
| 4,061,898 | 12/1977 | Murray et al. . |
| 4,147,921 | 4/1979 | Walter et al. . |
| 4,382,446 | 5/1983 | Truelock et al. ......................... 607/110 |
| 4,459,471 | 7/1984 | Hulett et al. ........................ 607/110 X |
| 4,512,830 | 4/1985 | Hulett et al. . |
| 4,552,149 | 11/1985 | Tatsuki .................................. 607/110 |
| 4,671,267 | 6/1987 | Stout . |
| 4,765,338 | 8/1988 | Turner et al. ........................... 607/110 |
| 5,119,812 | 6/1992 | Angelo .................................... 607/109 |
| 5,129,391 | 7/1992 | Brodsky et al. ....................... 607/110 |
| 5,314,005 | 5/1994 | Dobry .................................. 607/114 X |

OTHER PUBLICATIONS

Elasto–Gel Therapy Products Brochure, three pages.

*Primary Examiner*—Angela D. Sykes

[57] ABSTRACT

A thermal transfer hair treatment cap includes a liner having a plurality of pockets containing heat retaining gel and a decorative outer covering encompassing the liner. The gel is heatable in a conventional microwave oven, and the cap is configured to loosely capture and contact the hair of a user to transfer moist heat to the hair after the application of a conditioning composition to the hair.

5 Claims, 2 Drawing Sheets

THERMAL TRANSFER HAIR TREATMENT CAP

BACKGROUND OF THE INVENTION

1. Field of the Invention

The present invention relates to thermal transfer devices and, more particularly, to thermal transfer caps for applying moist heat to hair of an individual and to a method of conditioning hair utilizing a thermal transfer cap.

2. Discussion of the Prior Art

It is known that an application of moist heat to hair assists in the conditioning and repair of damaged hair. Specifically, it is desirable to apply heat to hair that is being conditioned such that the hair receives a full, deep conditioning treatment. By conditioning treatment is meant that a conditioner, such as an oil treatment composition or a commercially available conditioning composition, is applied to the hair and allowed to remain thereon for a length of time such that the beneficial effects of the composition are imparted to the hair. In the past, moist heat has been applied to hair during a conditioning process by wrapping heated, damp towels around the head. This method of applying moist heat to the hair has the disadvantages of difficult securement of the towel around the head resulting in inadvertent separation of the towel from the head, of being unsightly and unattractive and of being messy, ungainly and cumbersome.

To circumvent the disadvantages inherent in the use of a heated, damp towel for applying moist heat to the hair, heated air from a hair dryer is commonly substituted. However, the individual using the hair dryer must remain in the vicinity of the hair dryer thus impeding mobility of the individual during the conditioning process. More importantly, the heated air generated by the hair dryer has a drying effect which hinders the conditioning and repair process and, therefore, is inferior to moist heat applied to the hair.

Several devices have been created to subject an individual's head to raised and/or reduced temperatures. However, such devices have essentially been designed for heating or cooling the scalp, for example, for use by cancer chemotherapy patients to cool the scalp to prevent hair loss and to relieve headaches, high fever, heat stroke and hypothermia, do not fully accommodate an entire head of hair, and/or also require a close fit to apply pressure as well as heat or cold. U.S. Pat. Nos. 3,463,161 to Andrassy, 4,382,446 to Truelock et al, 4,552,149 to Tatsuki, 4,765,338 to Turner et al, and 5,129,391 to Brodsky et al and the gel-filled "cranial cap" manufactured by Southwest Technologies, Inc., 2018 Baltimore, Kansas City, Mo. 64108 are exemplary of such devices.

U.S. Pat. Nos. 1,710,882 to Larson, 1,737,460 to Johnson, 1,751,573 to Bishinger, 2,431,882 to Morten, 2,488,793 to Amerkan, 2,493,363 to Sapp, 2,680,305 and 2,718,068 to Reed, 2,745,192 to Crise, 2,945,115 to Weitzeh, 3,437,095 to Scott et al, 3,988,568 to Mantell, 4,061,898 to Murray et al, 4,147,921 to Walter et al and 4,459,471 and 4,512,830 to Hulett et al are representative of caps incorporating electrical heating elements therein for drying and/or treating hair. U.S. Pat. Nos. 2,420,358 to Culligan et al, 2,453,179 to Austin, 2,470,833 to Moore, 2,497,301 to Farmer, 2,804,695, 2,915,494 to Runci and 3,320,682 to Sleiman are representative of hair drying caps incorporating chemical compositions, such as silica gels or granular materials reactivated by heat after use. U.S. Pat. No. 2,783,806 is representative of caps containing heat retaining materials to be worn during hot oil treatments to provide heat to the scalp and hair. The above caps have the disadvantages of not supplying moist heat sufficient to effectively enhance hair conditioning treatments, not conforming to shapes required to accommodate hair of varying shapes and lengths without pressure, being difficult and expensive to manufacture, requiring special care in handling, use and storage and/or limiting mobility of the user.

SUMMARY OF THE INVENTION

Accordingly, it is a primary object of the present invention to provide a thermal transfer hair treatment cap overcoming the aforementioned disadvantages of the prior art.

Another object of the present invention is to enhance conditioning treatment of hair by application of moist heat after application of a conditioner thereto.

A further object of the present invention is to construct a thermal transfer hair treatment cap positionable upon the head of an individual to accommodate hair in various shapes and sizes.

An additional object of the present invention is to apply moist heat to an individual's hair in a quick, simple and efficient manner without reducing mobility of the individual.

The present invention has another object in that the thermal transfer hair treatment cap is formed of a plurality of cells of a microwave-heatable gel to allow the cap to be heated within a conventional microwave oven and to permit the gel-containing cells to articulate relative to each other to accommodate heads of hair of varying shapes and sizes.

The present invention is generally characterized in a thermal transfer hair treatment cap including a liner having a plurality of pockets formed therein and being positionable upon a head of a user to contact hair of the user, the plurality of pockets including a first group of pockets arranged to contact hair on the top and sides of the head and a second group of pockets arranged to contact hair on the back of the head, a plurality of microwave heatable gel units each positioned within one of the pockets; and an outer decorative covering coupled to the liner.

The present invention is further generally characterized in a method of conditioning hair utilizing a thermal transfer cap having cells containing gel capable of being heated by microwave radiation and storing the heat comprising the steps of applying a conditioning composition to the hair, heating the thermal transfer cap by exposing the cap to microwave radiation and loosely positioning the heated thermal transfer cap on the head in contact with the hair to apply moist heat to the hair.

Some of the advantages of the present invention over the prior art are increased mobility for the user, attractive appearance, heating of the cap can be quickly accomplished with a conventional microwave oven, and the gel-containing liner is detachable from the outer covering to allow the covering to be washed.

Other objects and advantages of the present invention will become apparent from the following description of the preferred embodiment taken in conjunction with the accompanying drawings.

DESCRIPTION OF THE PREFERRED EMBODIMENTS

Figure 1:
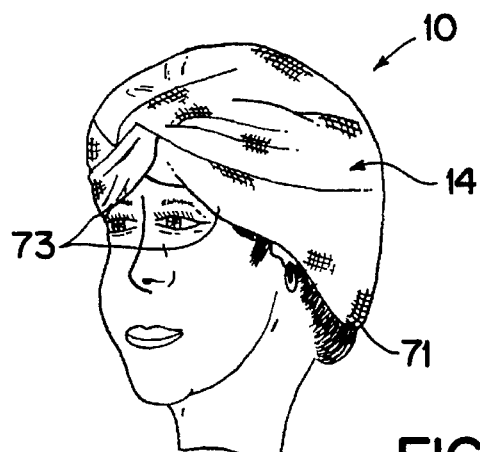
FIG. 1 is a perspective view of a thermal transfer hair treatment cap positioned on a user in accordance with the present invention.
Figure 2:
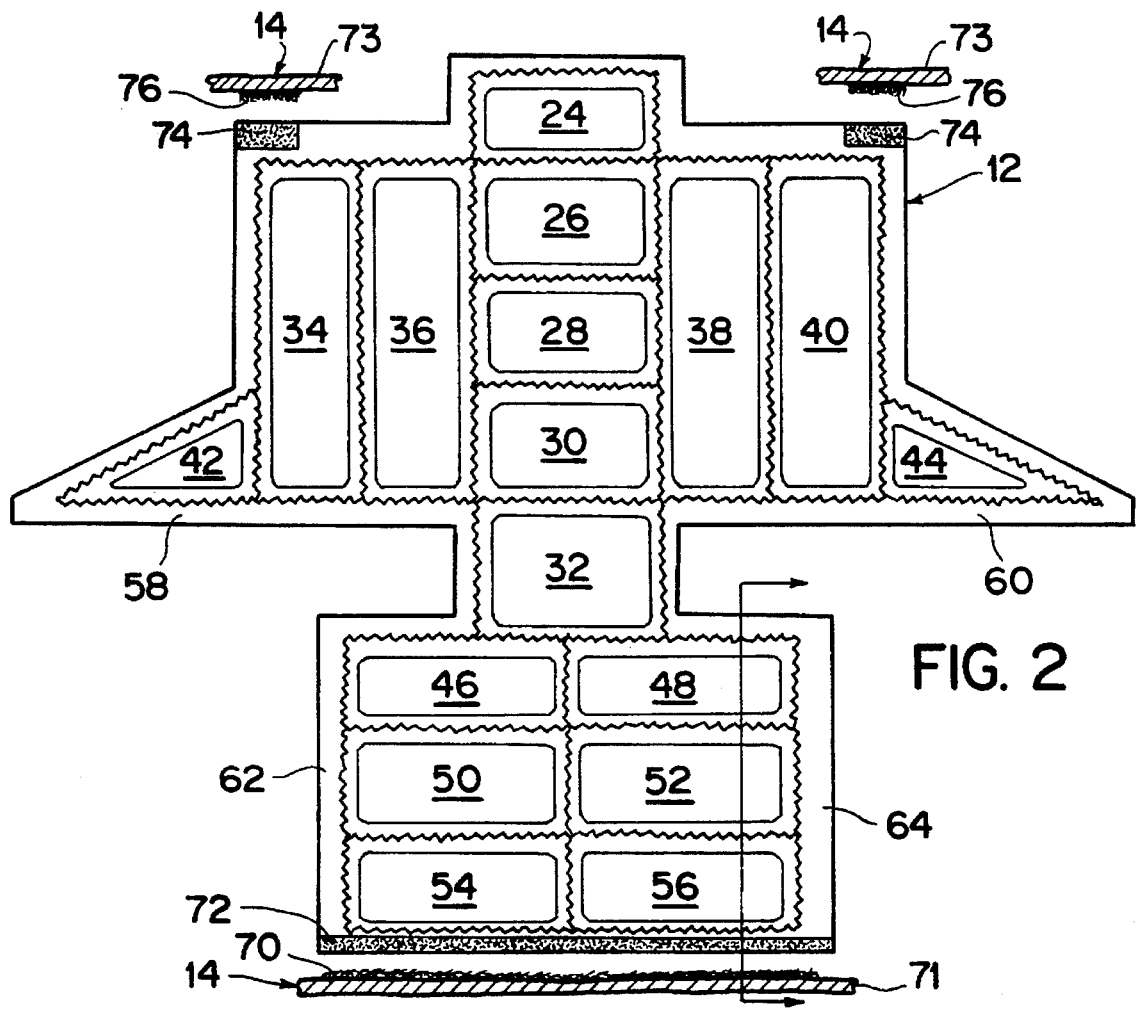
FIG. 2 is a plan view of a gel-containing liner of the thermal transfer hair treatment cap of the present invention.
Figure 4:
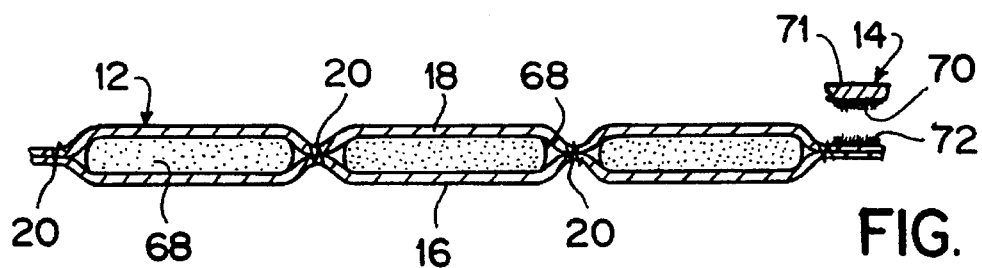
FIG. 4 is a cross-section taken along line 4—4 of FIG. 2.

A thermal transfer hair treatment cap 10 according to the present invention is formed of a gel-containing liner 12 detachably secured to an outer covering 14 having the configuration of a turban to be positioned on the head of a user to have a decorative, attractive appearance as shown in FIG. 1. As shown in FIGS. 2 and 4, the liner 12 is formed of an inner web 16 and an outer web 18 with the substantially similarly configured inner and outer webs sewn or otherwise secured or joined together at seams 20 to define a plurality of gel-containing cells or pockets within the liner. The arrangement of gel-containing cells or pockets includes a top group of pockets 24, 26, 28, 30 and 32 of a substantially rectangular configuration defined seams by 20 such that longitudinal sides of the top pockets are positioned adjacent longitudinal sides of adjoining top pockets. The liner 12 further includes a plurality of substantially rectangularly shaped side pockets 34, 36, 38 and 40 and two triangularly shaped pockets 42 and 44. The side pockets are arranged in laterally extending pairs on opposed, transverse sides of the top pockets and are positioned with inner longitudinal sides of the side pockets 36 and 38 adjacent the transverse sides of the top pockets and the outer side pockets 34 and 40 positioned adjacent outboard longitudinal sides of the side pockets 36 and 38, respectively. Positioned adjacent outboard longitudinal sides of the side pockets 34 and 40 are the respective triangularly shaped pockets 42 and 44 joined to the outboard longitudinal side of the respective side pockets 34, 40 at a transverse side of each triangularly-shaped side pocket. Positioned below the lowermost top pocket 32 is a group of rear pockets 46, 48, 50, 52, 54 and 56 of substantially rectangular shape similarly defined by the seams 20 securing the webs 16, 18 together. The rear pockets are positioned with transverse sides thereof joined in pairs and longitudinal sides of each rear pocket joined in pairs with the lower longitudinal side of the top pocket 32 being positioned adjacent and centered between the rear pockets 46, 48.

The liner 12, when positioned flat as shown in FIG. 2, is substantially symmetrical and reversible. By symmetrical and reversible is meant that the inner web 16 and the outer web 18 are substantially identical in shape such that they are interchangeable. The liner 12 may be constructed of any substantially flexible material, and is preferably constructed of a cotton and lycra fabric having ninety to ninety-five percent cotton content with a remaining content formed of lycra. A cotton-lycra fabric suitable for use with the present invention is available from Eclat Textile Company, Ltd., 250 North Puente Avenue, City of Industry, Calif.

Figure 3:
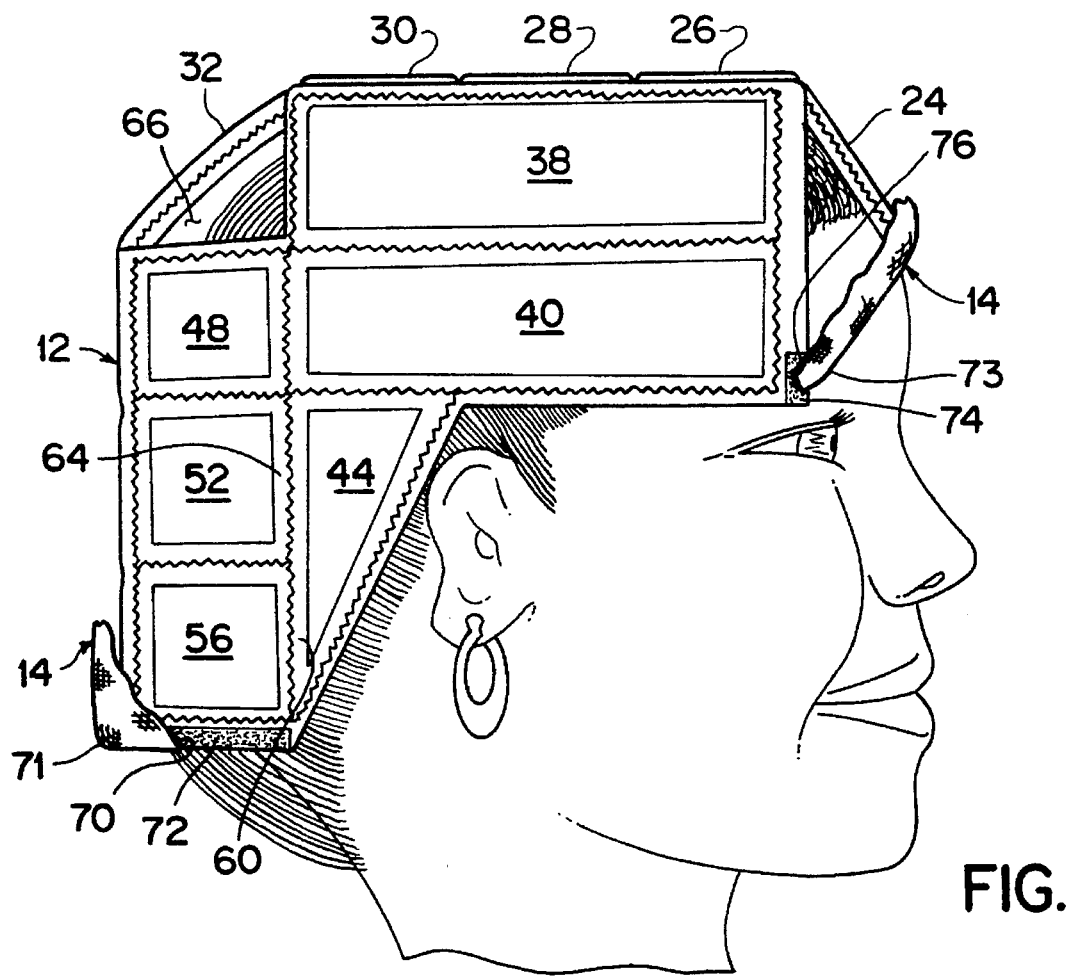
FIG. 3 is a side elevation view of the liner in position on a user with the outer covering broken away.

To conform the liner 12 to the shape of a head, as illustrated in FIG. 3, edges or margins 58 and 60 of respective triangular side pockets 42 and 44 are joined to respective edges or margins 62 and 64 along opposed transverse sides of the rear pockets. Such joining may be accomplished through stitching, bonding, adhesives or other similar fabric joining means, with the resultant joint positioning the rear pockets 46 and 48 in abutting relationship with respective side pockets 34 and 40, and the remaining rear pockets 50, 54 and 52, 56 in abutting relationship with longitudinal sides of respective triangular side pockets 42 and 44. As can now be readily ascertained from the illustration of FIG. 3, the triangular shape of the side pockets 42, 44 allows the cap 10 to closely contact hair positioned posteriorly of the ear along the nape of the neck without interfering with the ear. Specifically, the triangular shape of the side pockets 42 and 44 facilitates a more complete application of heat to hair located immediately behind the ears, and triangular spaces 66 are formed on opposite sides of the liner at the back of the head to permit the liner to conform to various sizes and shapes of heads and hair, the spaces 66 being bounded by the edges of pockets 32, 36 and 46 and 32, 38 and 48, respectively. The seams 20 act as hinge-like joints to allow the pockets to articulate relative to each other and conform to the shape of a head and hair on which the cap 10 is positioned, and the free motion of the front top pocket 24 to be variably spaced from pockets 36 and 38 adjacent the temple of a user, the variable spaces 66 created adjacent pocket 32 adjacent the back of the head and the articulation between adjacent pockets permit the cap to accommodate varying sizes and shapes of heads of hair while assuring contact with hair at the top of the head and the back of the head as well as along the sides and adjacent the ears.

The cells or pockets of the liner 12 contain a gel 68 formed of a composition capable of storing heat generated by microwaves such that the gel can be heated in a conventional microwave oven. A preferred gel 68 for use with the present invention is of the type sold under the trademark ELASTO-GEL by Southwest Technologies, Inc., 2018 Baltimore, Kansas City, Mo. 64108. Attention is also directed to U.S. Pat. No. 4,671,267 to Stout which discloses a method for making a gel useful with the present invention. The gel is positioned in the pockets of the liner after being poured into molds to form shaped gel masses or units of rectangular and triangular configurations corresponding in size to smaller rectangular pockets 24, 26, 28, 30, 32, 46, 48, 50, 52, 54 and 56, larger rectangular pockets 34, 36, 38 and 40 and triangular pockets 42 and 44. The gel units are initially placed on one liner web and then the other liner web is secured thereto to form the seams 20 defining each pocket by stitching, bonding, adhesive or the like. The gel units are held in place by adhering to the liner as well as being captured in the cells or pockets of the liner. In a preferred embodiment, the smaller rectangular pockets are approximately 1⅝" by 3⅜", the larger rectangular pockets are approximately 1⅜" by 5¼", the triangular pockets are approximately 1½" by 3⅜" by 3 ¹¹⁄₁₆" and the thickness or depth of each gel unit is approximately ⅜".

The outer covering 14 extends around the liner 12 and serves to insulate the liner to reduce heat losses to ambient air and to provide a decorative, attractive covering resembling a turban and formed of a terry cloth material. An example of a suitable terry cloth material is a stretch terry cloth made of eighty percent cotton and twenty percent polyester available from Hardwick-Knitted Fabrics, Inc., 101 Fifth Avenue, New York, N.Y. 10018, as well as from Absolutely Terry, Inc., 110 West 40th Street, New York, N.Y. 10018. While the outer covering 14 configured as a turban be worn by either males or females, it is contemplated that a more suitable male outer covering 14 could be shaped to resemble an African cultural dress cap. The covering 14 is detachably secured to the liner 12 at the rear by a fastener strip 70 secured adjacent the bottom 71 of the covering 14 adapted to be positioned adjacent the nape of the neck and to engage a fastener strip 72 secured to the margin of liner 12 adjacent rear pockets 54 and 56. Similarly, at the front of the cap, fastener strips 74 are secured to covering 14 at spaced, opposing positions 73 adapted to be positioned adjacent the temple and to engage spaced fastener strips 76 secured to the margin of liner 12 at opposing corners adjacent pockets 34 and 40. The fastener strips are preferably formed of complementary hook and loop fasteners, such as Velcro.

In use, the cap 10 is positioned in a conventional microwave oven and heated for approximately two minutes. In as much as the wattage or heating ability of different microwave ovens varies considerably, the heating time may vary; and, in practice, it is preferable to heat the cap on opposite sides. The cap is preferably heated with the liner in the covering; however, the liner can be heated separately and then installed or attached to the covering. Regardless of the microwave oven utilized to heat the device, it is preferable that the cap 10 be inverted once during the heating process to ensure uniform heating. The cap 10 should be heated to a predetermined temperature substantially above ambient room temperature but less than a temperature that would be detrimental to the hair or scalp. If the hair extends below the neck, the hair is lifted and positioned upon the head for reception within the cap 10. After application of a conditioning treatment to the hair, the heated cap is positioned on the head as illustrated in FIG. 1; and the user is free to move about while the cap 10 transfers moist heat to the hair resulting in a deep conditioning of the hair. By deep conditioning is meant that the conditioner will be more effectively absorbed within the hair in the presence of the moist heat transferred by the cap 10. The cap 10 is left in place for a desired length of time, preferably approximately twenty minutes, with the cap being reheated during such time period if necessary. After the time has elapsed, the cap 10 is removed, and the conditioning process is continued in accordance with the instructions accompanying the conditioning composition, i.e. the conditioning composition is either removed through washing or allowed to remain on the hair.

The outer covering 14 can be easily separated from the liner 12 by detaching the fastener strips at the front and back of the cap such that the covering can be washed or cleaned, and the covering is simply reinstalled on the liner by fitting the covering over the liner and pressing the fastener strips together. Various styles of outer coverings can be interchangeable with a single liner allowing a user to produce different appearances by installing fastener strips at the same positions on the various styles.

In as much as the present invention is subject to many variations, modifications and changes in detail, the above description of the preferred embodiment is intended to be exemplary only and not limiting.

What is claimed is:

1. A thermal transfer hair treatment cap comprising:

a liner formed of an inner web and an outer web coupled together in a facing relationship to define a plurality of adjoining top pockets each having longitudinal sides and transverse sides with each longitudinal side of each top pocket being positioned adjacent the longitudinal side of an adjoining top pocket, a plurality of side pockets each having longitudinal sides and transverse sides with the longitudinal side of at least one side pocket being positioned adjacent an individual transverse side of at least one of said top pockets and the longitudinal side of at least another side pocket being positioned adjacent another individual transverse side of at least another of said top pockets, a plurality of triangularly shaped pockets each having a longitudinal side and a transverse side with said transverse side of each triangularly shaped pocket being positioned adjacent an outboard longitudinal side of one of said plurality of side pockets and a plurality of rear pockets each having longitudinal sides and transverse sides with said transverse sides of said rear pockets being joined together in pairs and with a remaining lower longitudinal side of one of said plurality of top pockets being positioned adjacent one of said longitudinal sides of at least one of said rear pockets, at least one of said transverse sides of said rear pockets being joined to said longitudinal side of one of said triangularly shaped pockets and at least another of said transverse sides of said rear pockets being joined to said longitudinal side of another one of said triangularly shaped pockets;

a plurality of gel units, each positioned within one of said pockets; and a decorative outer covering attached to and surrounding said liner.

2. A thermal transfer hair treatment cap as recited in claim 1 wherein said gel units are heatable by microwave radiation to store heat.

3. A thermal transfer hair treatment cap as recited in claim 2 wherein said outer covering is configured as a turban.

4. A thermal transfer hair treatment cap as recited in claim 3 wherein said pockets are formed by stitched seams joining said inner and outer webs to permit said pockets to articulate relative to each other.

5. A thermal transfer hair treatment cap as recited in claim 1 wherein said gel units are positioned in all of said pockets.

\* \* \* \* \*